United States Patent [19]

Morris

[11] Patent Number: 4,586,498
[45] Date of Patent: May 6, 1986

[54] SURGICAL DRAPE WITH ARM BOARD COVER

[75] Inventor: Henrietta K. Morris, Arlington, Tex.

[73] Assignee: Surgikos, Inc., Arlington, Tex.

[21] Appl. No.: 604,109

[22] Filed: Apr. 26, 1984

[51] Int. Cl.$^4$ ............................................. A61B 19/06
[52] U.S. Cl. ............................. 128/132 D; 128/132 R
[58] Field of Search ......................... 128/132 D, 132 R

[56] References Cited

U.S. PATENT DOCUMENTS

| | | | |
|---|---|---|---|
| 26,759 | 1/1970 | Melges | 128/132 D |
| 2,593,121 | 4/1952 | Pjorup | 128/132 D |
| 3,750,663 | 8/1973 | Collins | 128/132 D |
| 3,856,006 | 12/1974 | Krzewinski | 128/132 D |
| 4,027,665 | 6/1977 | Scrivens | 128/132 D |
| 4,336,797 | 6/1982 | Latucca et al. | 128/132 D |
| 4,489,720 | 12/1984 | Morris | 128/132 D |

Primary Examiner—Paul J. Hirsch
Assistant Examiner—John G. Weiss
Attorney, Agent, or Firm—Michael Q. Tatlow

[57] ABSTRACT

A surgical drape having arm board covers is disclosed. The arm board covers are formed in an arm board portion of the drape by cutting and folding the drape material so that it may be attached to the body portion of the drape along a single line of attachment. The drape may also provide leg covering elements integral with the body portion of the drape.

5 Claims, 12 Drawing Figures

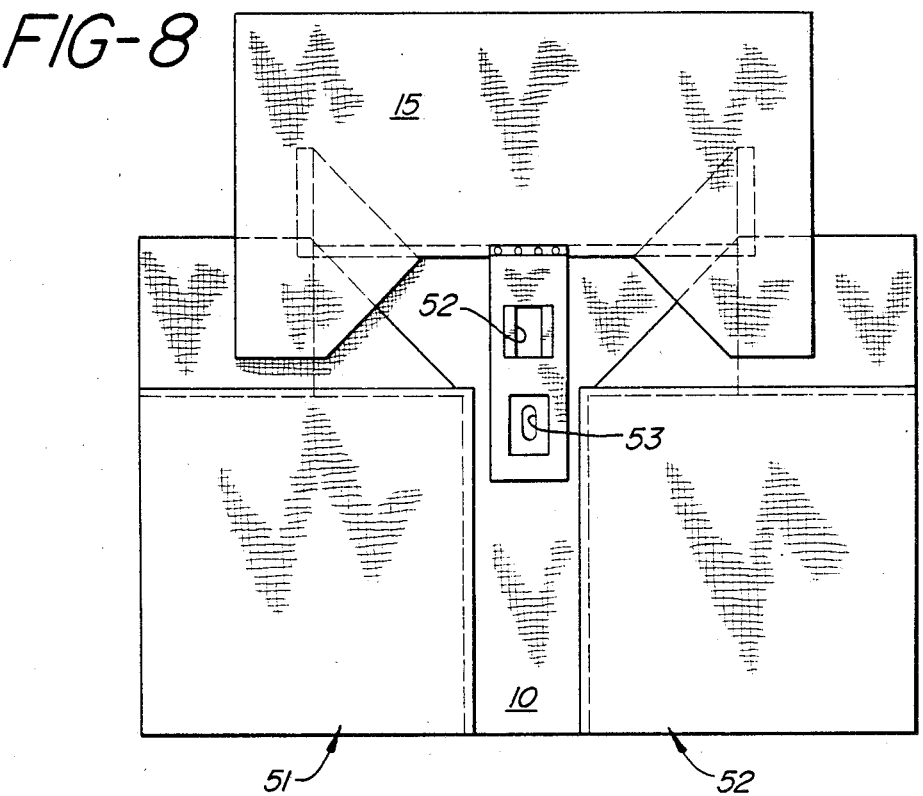
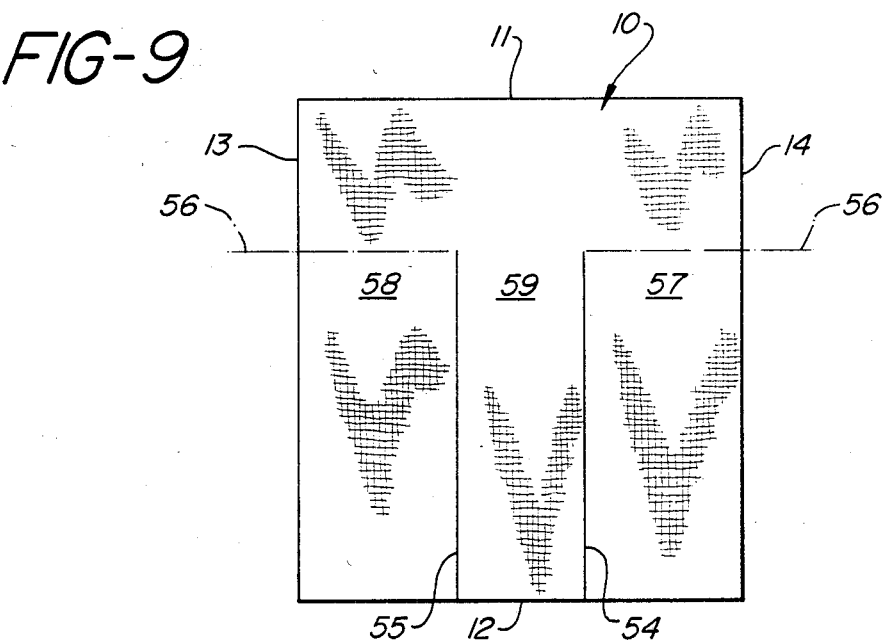

SURGICAL DRAPE WITH ARM BOARD COVER

BACKGROUND OF THE INVENTION

1. Field of the Invention

The present invention relates to surgical drapes and, more particularly, to a surgical drape providing an arm board cover to cover the arms of a patient when the patient is reclining on an operating room table having arm boards extending laterally from the table. Surgical drapes of this type are frequently referred to as T-shaped surgical drapes, as the main portion of the drape has a portion extending across the top of the drape which is wider than the width of the main portion of the drape and is in the shape of a "T". An additional embodiment of the present invention also provides a surgical drape with integral leg coverings or leg drapes.

2. Description of the Prior Art

Examples of drapes with arm board covers are disclosed in U.S. Pat. Nos. 3,856,005 and 3,856,006. The surgical drape shown in U.S. Pat. No. 3,856,005 is a laparotomy sheet with an upper, T-shaped portion to cover the arms of a patient. There is a gusset in the drape in the area where the wing or arm sections of the drape meet the main body of the drape. The gusset is made of additional drape material, and it enables the peripheral edge of the wing or arm sections to hang substantially vertically downward over the edge of the operating room table when the drape is in use.

The drape shown in U.S. Pat. No. 3,856,006 consists of a main body to cover the torso of the patient and the patient's legs and a T-shaped portion which will cover the arm boards of the operating room table and the arms of the patient. The arm boards have flaps attached to the lower edge of the T-shaped portion or wing portion of the drape to allow this portion to hang down over the edge of the arm board when the drape is in use.

Although the drapes of the prior art provide an improved coverage of the arms of a patient, they suffer from certain difficulties. The drapes require multiple manufacturing steps to secure the extra material in the proper location, and the construction of the drapes also results in an exposed seam between the added pieces of material on the main body of the drape. The exposed seam could provide a possible path for the passage of bacteria through any opening in the seam, and the seams were the weakest point in the drape construction.

Prior art drapes which disclose leg coverings which are integral or attached to body covering portions of a drape include the following:

U.S. Pat. No. 3,182,656 discloses a drape constructed with a central component to cover the torso of the patient and a pair of segmental shaped components to cover the legs of the patient. The drape disclosed is quite complicated to manufacture and, because of its complex shape, it is difficult to aseptically place on the patient in the operating room.

U.S. Pat. No. 2,593,121 discloses a medical examination drape with leg covering portions. This drape would not provide adequate coverage of the patient during a surgical procedure unless the drape was made using excess amounts of fabric.

U.S. Pat. No. 3,251,360 discloses a one-piece gynecology or lithotomy drape with integral leg converings. The drape of this patent does not provide the degree of coverage of the patient's legs and torso without use of excess fabric.

U.S. Pat. No. 3,750,663 discloses a lithotomy sheet which is similar to the lithotomy sheet disclosed in U.S. Pat. No. 3,251,360.

SUMMARY OF THE INVENTION

The present invention provides a T-shaped or winged surgical drape for use with an operating table having arm boards extending laterally therefrom. The T-shaped or wing portion of the drape is attached to the main portion of the drape along a single seam, which is in a position away from a point in which an operating room staff member could tear the seam during the surgical procedure. The drape may be readily assembled from two pieces of nonwoven fabric or other material and secured along a single continuous seam.

An additional embodiment of the present invention provides a drape with integral leg coverings. The leg coverings can be manufactured with a minimum of manipulative steps and with optimum use of fabric.

BRIEF DESCRIPTION OF THE DRAWINGS

The invention will be more fully understood by reference to the attached drawings which show illustrative embodiments of the invention.

FIG. 8 shows a top plan view of a drape of FIG. 1 with integral leg coverings.

FIGS. 9–12 show the cutting, folding and attachment sequences to form the leg coverings shown in FIG. 8.

DETAILED DESCRIPTION OF THE INVENTION

Figure 1:
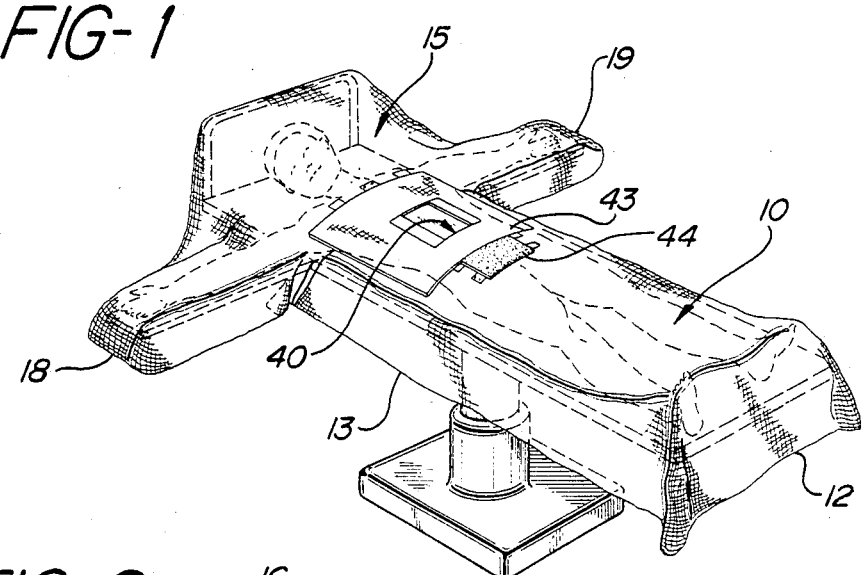
FIG. 1 is an isometric view of the surgical drape of the present invention in place on a patient.

FIG. 1 shows the drape of the present invention covering a patient in a laparotomy position on an operating room table.

Figure 2:
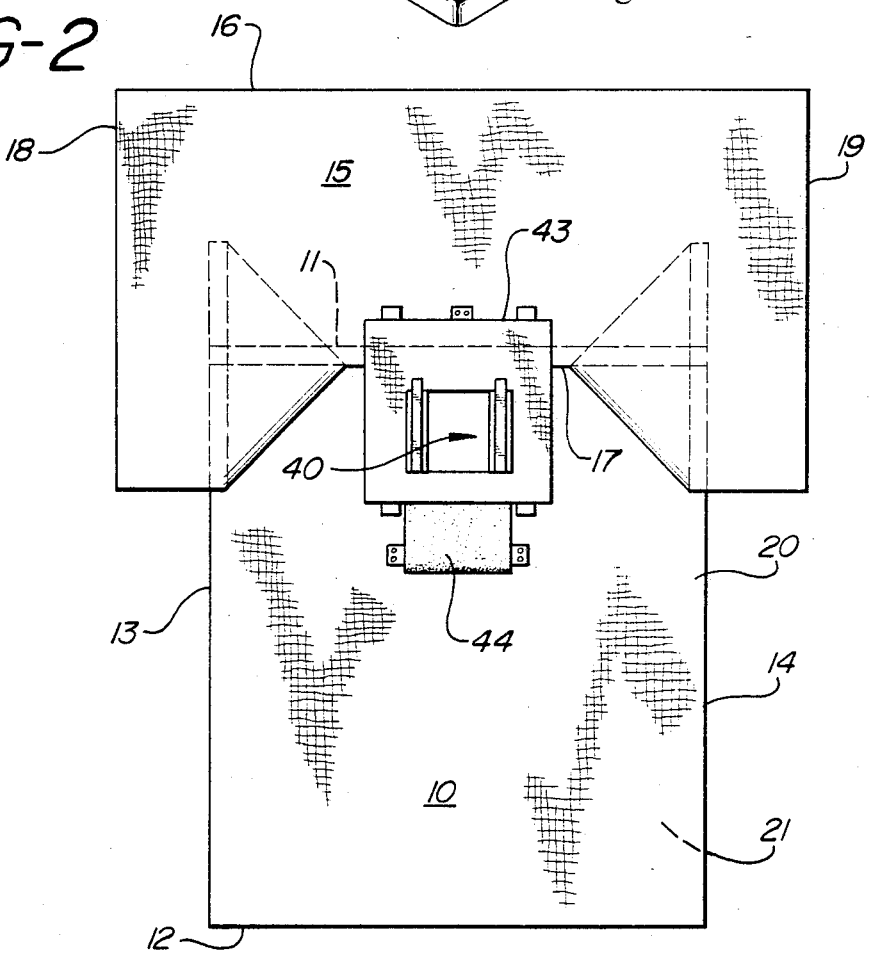
FIG. 2 is a top plan view of the surgical drape of the present invention.
Figure 3:
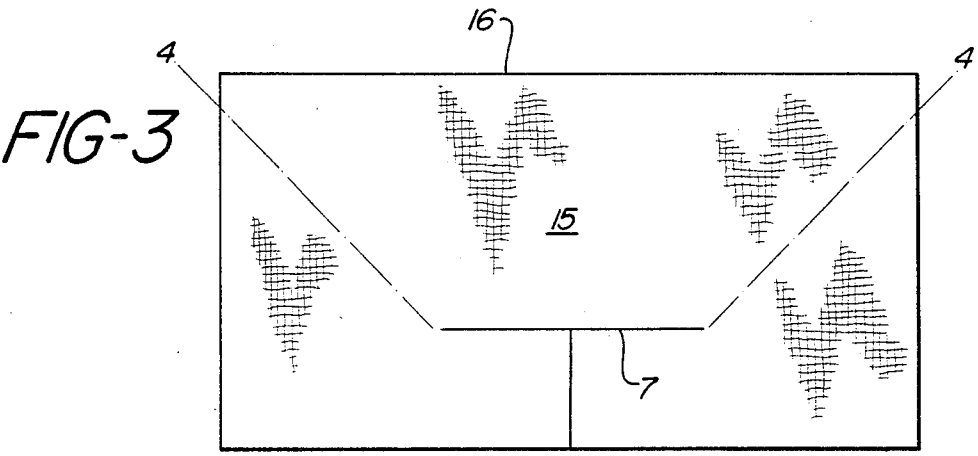
FIG. 3 is a plan view of the arm board section of the drape showing the cutting sequence and fold lines in the drape.
Figure 4:
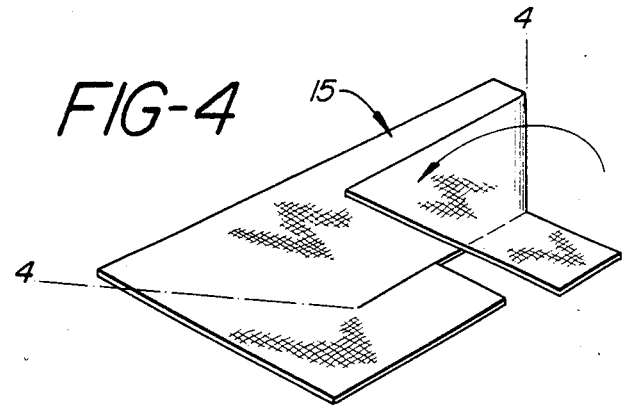
FIG. 4 shows the drape of FIG. 3 folded along one of the fold lines 4—4.

FIG. 2 shows a top plan view of the completed surgical drape of the present invention.

The drape is constructed of a nonwoven fabric or other material which has the desired properties for a surgical drape. These properties are repellency to water and other liquids commonly found in the operating room, such as alcohol and antiseptic solutions, and a relatively low cost for the fabric material, since the majority of surgical drapes in use today are single use drapes, which are disposed of after a single use.

The drape shown in FIG. 2 has a body portion 10 which is used to cover the torso and legs of the patient when the drape is in use with a patient in a laparotomy position. In the laparotomy position, the patient's feet are resting on the operating table at the same level as the torso. The body portion has a top edge 11, a bottom edge 12 and two opposing side edges 13 and 14. There is a wing portion or T-shaped portion 15 attached to the top edge of the body portion. The wing portion also has a top edge 16, a bottom edge 17 and two oppsing side edges 18 and 19.

The upper surface of the drape 20 is that surface which is facing the surgical team when the drape is in use. The lower surface 21 is the surface which is in direct contact with the patient.

Figure 5:
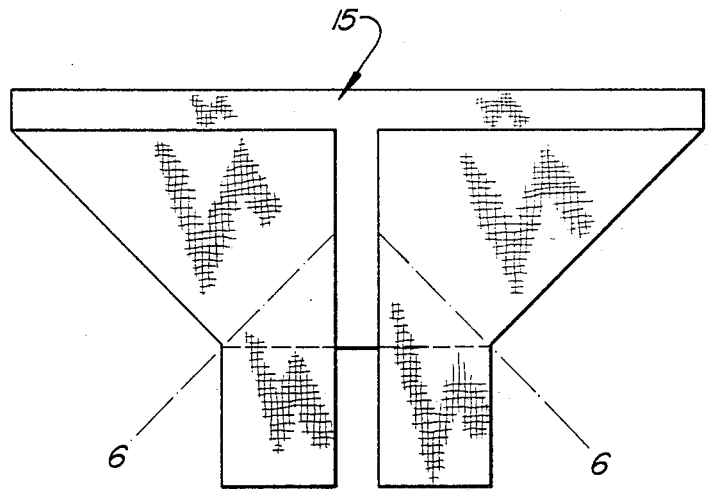
FIG. 5 shows the upper portion of the drape folded along both fold lines 4—4.
Figure 6:
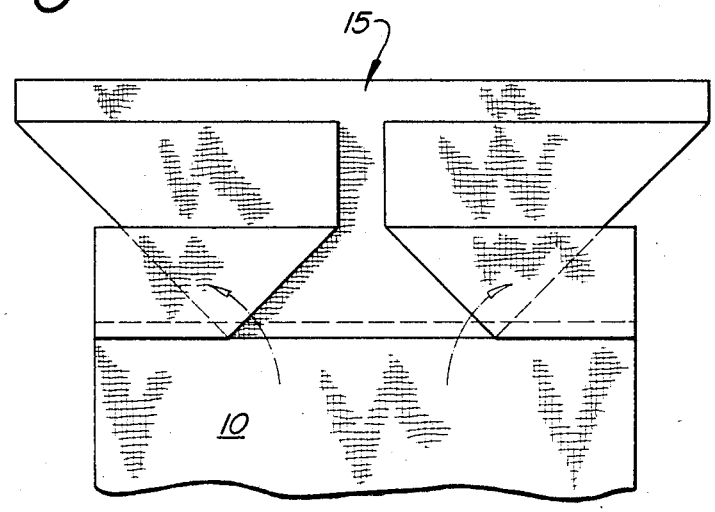
FIG. 6 shows the upper portion of the drape folded along fold lines 6—6 of FIG. 5 of the drape.
Figure 7:
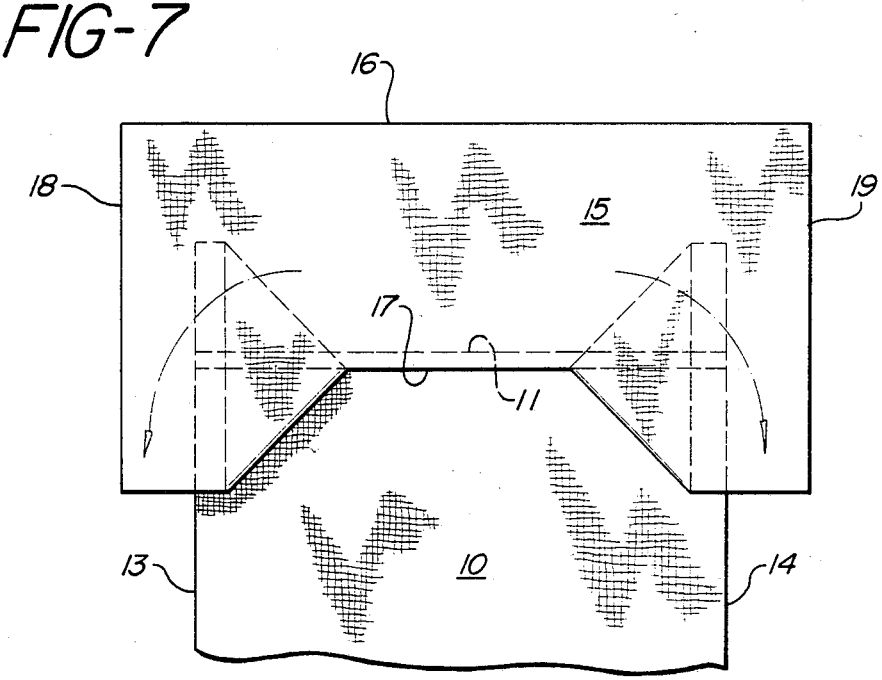
FIG. 7 shows the final fold in the sequence.
Figure 10:
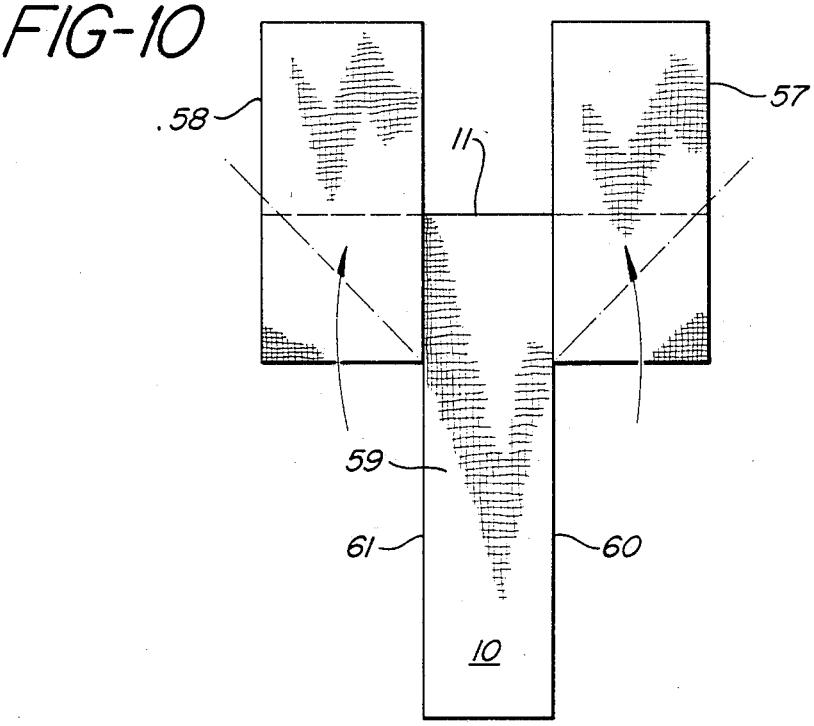

The sequence of forming the wing shaped portion 15 of the present surgical drape can be seen from FIGS. 3, 4, 5 and 6 of the drawings. A generally rectangular sheet is cut from the lower edge to and along a transversely-extending line in the mid-portion of the drape which extends for about ⅓ of the width of the drape. The drape is then foled at a 45° angle from the end of the transversely-extending cut to form the configuration shown in FIGS. 4 and 5. The drape is then folded again on 45° lines extending from the ends of the transversely-extending slit at a 45° angle, which is 90° from the 45° angle of the first fold. The second fold lines are shown in FIG. 5. The result of this folding sequence is shown in FIG. 6. This folding sequence provides a single edge which may be attached to the top edge of the main body portion of the drape by adhesive. The single adhesive line enables the drape of the present invention to be assembled with a minimum of manipulative steps, as there is only a single line joining the body portion to the wing portion of the drape. The wing portion may be attached on either the upper or the lower surface of the body portion 10 of the drape.

There is shown in FIGS. 1 and 2 various optional construction features of a drape of this type. These features include a fenestration 40 through the body of the drape. The fenestration shown in FIG. 2 is for a surgical procedure in the abdominal area of the patient. The drape of the present invention may have fenestrations in other locations of the drape for other surgical procedures. For example, there may be a slit in the drape from one or both side edges of the drape when the drape is to be used for cardiovascular procedures. The particular placement of the fenestration is determined by the surgical procedure for which the drape will be employed. The surgical procedures are usually performed through the pre-formed fenestration of the surgical drape. The fenestration is usually through a reinforcing element 43 which is secured to the upper surface of the drape. The reinforcing element can be constructed of an absorbent fabric material which is backed with an impervious plastic film. The use of the absorbent upper surface provides capacity for liquid to be absorbed during the surgical procedure, and the use of the impervious plastic film on the underside of the reinforcement prevents that liquid from penetrating through the surgical drape and possibly contaminating the patient at the surgical wound site. The reinforcement area 43 may have tubing tabs attached to it at various locations around the periphery of the reinforcement area. In addition, there may be clamping tabs also secured around the periphery of the reinforcement area. These clamping tabs are free to move up and down and provide a site on which various materials can be clamped to the drape without the fear of penetrating the drape with a clamp. There may also be an instrument pad 44 to provide a nonslip surface to deposit instruments during the surgical procedure.

FIG. 8 shows the drape of the present invention modified to include vertical leg coverings. The integral leg coverings are desirable in surgical drapes used in gynecology and lithotomy procedures when the patient's legs are held in an elevated position above the level of the operating table. The patient's legs are set in stirrups in such procedures. The legs and the supporting structure for the stirrups must be entirely covered by the drape. The drape shown in FIG. 8 is for a laparoscopy procedure. The upper portion or arm board portion of the drape is identical to that previously described.

The body portion 10 of the drape of FIG. 8 includes the integral leg coverings 50 and 51. The body portion 10 includes a reinforcing area 43. There are two fenestrations 52 and 53 through the reinforcing area.

The sequence of forming the integral leg coverings is shown in FIGS. 9–12. A rectangular sheet which will form the body portion of the drape has a top edge 11, a bottom edge 12 and opposed side edges 13 and 14. The sheet is cut from the bottom edge 12 along two lines 54 and 55, which are parallel to the side edges, to a line 56 to form two side segments 57 and 58 and a central segment 59. The side segments are then folded around the fold line 56 to form the configuration shown in FIG. 10. Side segments 57 and 58 are each folded along a line extending at an angle of 45° from the intersection of the side edges 60 and 61 of the central segment 59 and the fold line 56.

Figure 11:
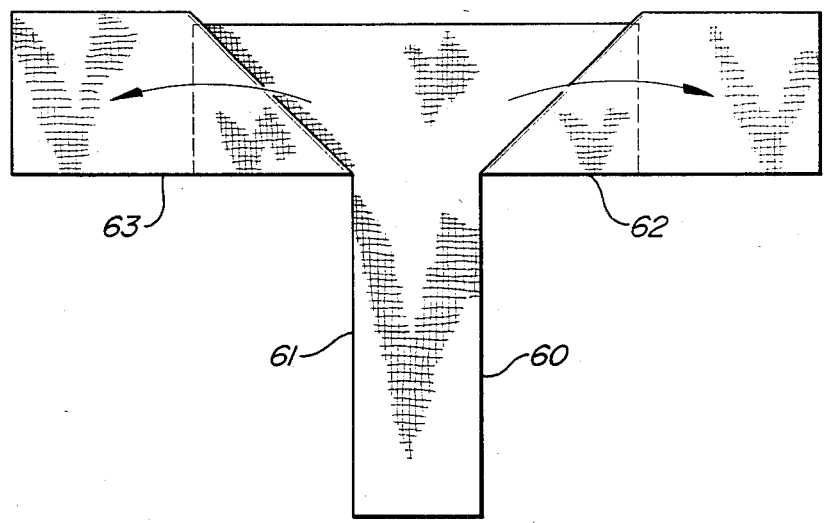
Figure 12:
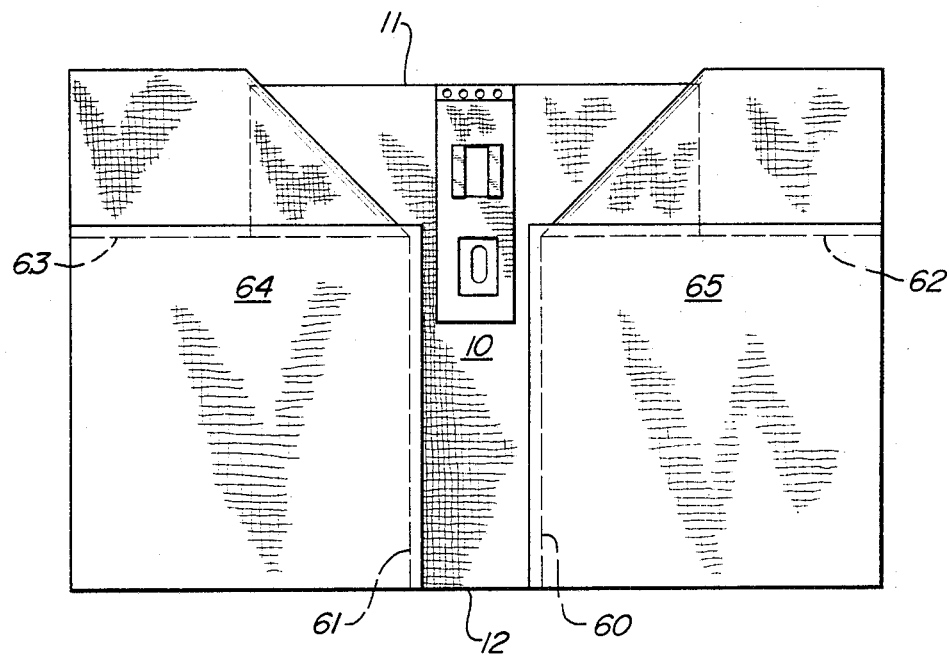

The partially formed drape is shown in FIG. 11. The side edges 60 and 61 of the central segment and the lower edges 62 and 63 of the original side segments now are generally perpendicular to each other. Two rectangular pieces 64 and 65 of drape fabric are then secured to the drape overlapping the side edges 61 an 60 of the central segment and the lower edges 62 and 63 of the side segments. The resulting drape is shown in FIG. 12. The leg coverings thus formed provide adequate coverage of a patient's legs.

I claim:

1. A surgical drape for use with an operating table having arm boards extending laterally therefrom, said drape comprising, when in a flat position, a generally rectangular body portion having a top edge, a bottom edge and two opposing side edges, a one-piece arm board portion having a top edge, a bottom edge and two opposing side edges and an upper surface and a lower surface, and said arm board portion being divided in width into a central area and two side areas, the bottom edge of the central area overlapping and being secured to the top edge of the body portion along a line of attachment, each of the side areas comprising a first segment underlying the upper surface of the drape and having a part which is secured to the top edge of the body portion on a continuation of the line of attachment of the central area and a second part which is integral with a second segment, said second segment overlying the first segment and forming the upper surface of the arm board portion, said first segment capable of unfolding to conform to the junction of the operating table and the arm boards of the operating table.

2. The surgical drape of claim 1 further comprising a fenestration in the body portion of the drape.

3. The surgical drape of claim 1 in which the body portion includes a leg-covering element on each of the side edges of the drape, each of said leg-covering elements comprising a first part integral with the body portion and triangular in shape and a second part integral with said first part and connected thereto along a fold line which is at a 45° angle, a third part which is secured to the body portion along a first attachment line and which is secured to the second part along a second attachment line which is at an angle 90° to the first attachment line.

4. A method of forming a surgical drape providing a generally rectangular sheet of drape material having an upper edge, a lower edge and two opposing side edges, making a cut from the lower edge inwardly of the sheet of material a distance of from ¼ to ⅓ of its dimension along a side edge, making a cut at 90° from the first cut in both directions to a distance approximately ¼ to ⅓ of the dimension along a top or bottom edge, folding the drape along lines extending at a 45° angle from both ends of the second cut so that the upper surfaces of material are in face-to-face contact, making a second 45° fold which is 90° from the first fold, securing the thus folded arm board portion of a drape to the top edge of the body portion of a surgical drape, along a continuous line of attachment and folding each of the side sections of the drape along the last fold line to form arm board covers in the drape.

5. The method of claim 4 in which the body portion of the drape is a generally rectangular sheet of material having a top edge, a bottom edge and two opposing side edges and is formed by cutting the sheet of material from the bottom edge of the drape along two lines parallel to the side edges to a distance of from ⅓ to ¾ of the dimension along the side edges, folding each of the segments formed by the cut along a line which is parallel to the top edge of the drape, folding each segment thus formed along a 45° angle extending from the end of the cut line, securing a generally rectangular piece of drape material to the body portion of the drape along the cut line extending from the bottom edge of the drape and along the lower edge of the portion folded at a 45° angle.

* * * * *